United States Patent [19]
D'Alise

[11] Patent Number: 5,755,574
[45] Date of Patent: May 26, 1998

[54] ENDOSSEOUS DENTAL IMPLANT AND METHOD OF MANUFACTURE

[76] Inventor: James V. D'Alise, 730 Pinecrest Ct., Hinsdale, Ill. 60521

[21] Appl. No.: 469,687

[22] Filed: Jun. 6, 1995

Related U.S. Application Data

[63] Continuation-in-part of Ser. No. 232,448, Apr. 21, 1994, Pat. No. 5,468,149.

[51] Int. Cl.$^6$ .................................................. A61C 8/00
[52] U.S. Cl. ........................................ 433/173; 433/174
[58] Field of Search ............................... 433/173, 174, 433/175, 176

[56] References Cited

U.S. PATENT DOCUMENTS

| | | | |
|---|---|---|---|
| 711,324 | 10/1902 | Lacy . | |
| 866,304 | 9/1907 | Roach . | |
| 2,112,007 | 3/1938 | Adams | 32/2 |
| 2,347,567 | 4/1944 | Kresse | 32/12 |
| 2,609,604 | 9/1952 | Sprague | 32/1 |
| 3,435,526 | 4/1969 | Brancato | 32/10 |
| 3,499,222 | 3/1970 | Linkow et al. | 32/10 |
| 3,732,621 | 5/1973 | Bostrom | 32/5 |
| 3,787,975 | 1/1974 | Zuest | 32/5 |
| 3,849,888 | 11/1974 | Linkow | 32/10 |
| 4,016,651 | 4/1977 | Kawahara | 32/10 |
| 4,109,383 | 8/1978 | Reed et al. | 32/10 |
| 4,177,562 | 12/1979 | Miller et al. | 433/174 |
| 4,180,910 | 1/1980 | Stranmann et al. | 433/173 |
| 4,187,609 | 2/1980 | Edelman | 433/176 |
| 4,195,367 | 4/1980 | Krams | 3/191 |
| 4,204,321 | 5/1980 | Scott | 433/177 |
| 4,259,072 | 3/1981 | Hirabayashi et al. | 433/173 |
| 4,290,755 | 9/1981 | Scott | 433/173 |
| 4,302,188 | 11/1981 | Driskell | 433/173 |
| 4,324,550 | 4/1982 | Reuther et al. | 433/174 |
| 4,334,865 | 6/1982 | Borle | 433/221 |
| 4,359,318 | 11/1982 | Gittleman | 433/173 |
| 4,416,629 | 11/1983 | Mozsary et al. | 433/174 |

(List continued on next page.)

FOREIGN PATENT DOCUMENTS

| | | |
|---|---|---|
| 0073177 | 8/1982 | European Pat. Off. . |
| 3423752 | 10/1985 | Germany . |
| 604674 | 9/1978 | Switzerland . |
| 660342 | 11/1951 | United Kingdom . |
| 757487 | 9/1956 | United Kingdom . |
| 937944 | 9/1963 | United Kingdom . |
| 968672 | 9/1964 | United Kingdom . |
| 1203093 | 8/1970 | United Kingdom . |
| 1291470 | 10/1972 | United Kingdom . |
| 1352188 | 5/1974 | United Kingdom . |
| 1544784 | 4/1979 | United Kingdom . |
| 1565178 | 4/1980 | United Kingdom . |
| 8601705 | 3/1986 | WIPO . |

OTHER PUBLICATIONS

The International Journal of Periodontics & Restorative Dentistry, vol. 9, No. 2, pp. 97–105 (1989).
Spectra–System® Abutments Brochure.
Component Assembly Sequence, ROOT GRAPHICS, Revised Parts Assembly Manual Apr. 1990.
ZEST® ANCHORS, Inc., Dental Attachment System.
Calcitek® OMNILOC®, Brochure.
"Implant Prosthodontics a Team Approach," Oral Implantology, vol. XII, No. 1, 1985.
"Osseointegrated Implants in the Treatment of the Edentulous Jaw," Branemark, P.-I., Hansson, B. et al., Scand.J.Plast.Reconstr. Surg. 11, Suppl. 16, (1977).
"Osseointegrated Titanium Implants," T. Albrektsson et al., Acta orthop. scand. 52, 155–170, 1981.

*Primary Examiner*—Nicholas D. Lucchesi
*Attorney, Agent, or Firm*—Jefferson Perkins; Foley & Lardner

[57] ABSTRACT

An endosseous dental implant system includes an endosseous implant body which is adaptable to receive either a screw-threaded abutment or a press-fit abutment base. An endosseous implant body replica and an impression pick-up are used in conjunction with the press-fit abutment base to get an exact translation of reference points of the implanted body from the patient's mouth to a model, where a dental prosthesis can be fashioned without prior art alignment problems.

26 Claims, 7 Drawing Sheets

U.S. PATENT DOCUMENTS

| | | | |
|---|---|---|---|
| 4,431,416 | 2/1984 | Niznick | 433/174 |
| 4,468,200 | 8/1984 | Munch | 433/174 |
| 4,488,875 | 12/1984 | Niznick | 433/173 |
| 4,552,532 | 11/1985 | Mozsary | 433/173 |
| 4,573,922 | 3/1986 | Bello | 433/176 |
| 4,624,673 | 11/1986 | Meyer | 623/16 |
| 4,626,214 | 12/1986 | Artal | 433/174 |
| 4,645,453 | 2/1987 | Niznick | 433/173 |
| 4,661,066 | 4/1987 | Linkow et al. | 433/176 |
| 4,668,191 | 5/1987 | Plischka | 433/174 |
| 4,713,004 | 12/1987 | Linkow et al. | 433/174 |
| 4,758,161 | 7/1988 | Niznick | 433/173 |
| 4,854,873 | 8/1989 | Linden | 433/173 |
| 4,960,381 | 10/1990 | Niznick | 433/174 |
| 5,062,800 | 11/1991 | Niznick | 433/229 |
| 5,076,788 | 12/1991 | Niznick | 433/173 |
| 5,078,607 | 1/1992 | Niznick | 433/174 |
| 5,092,771 | 3/1992 | Tatum, III | 433/173 |
| 5,238,405 | 8/1993 | Marlin | 433/173 |
| 5,302,126 | 4/1994 | Wimmer et al. | 433/173 |
| 5,376,004 | 12/1994 | Mena | 433/173 |

ENDOSSEOUS DENTAL IMPLANT AND METHOD OF MANUFACTURE

RELATED APPLICATIONS

This application is a continuation-in-part of application Ser. No. 08/232,448, filed Apr. 21, 1994 now U.S. Pat. No. 5,468,149. The parent application is hereby fully incorporated by reference.

TECHNICAL FIELD OF THE INVENTION

This invention is generally related to dental prostheses, and is specifically directed to an endosseous dental implant suitable for use with both screw-threaded and press-fit prosthetic abutments.

BACKGROUND OF THE INVENTION

Implanted prosthetic teeth conventionally have an endosseous implant body into which is inserted a head or abutment. The abutment base is used as a platform to create a prosthetic tooth, which usually has a gold or other metallic core and an white nonmetallic exterior. Dentists and dental manufacturers commonly supply and use different types of dental implant abutments, parts, screws, etc. to fabricate a dental prosthesis. The dental profession has available to it straight abutments, pre-angled abutments, and a loose-fitting, nonmachined plastic press-fit abutment. Frequently, the type of implant chosen depends on the placement of the implant body within the jaw bone itself.

Sometimes jaw bone topography, such as the shape or size, will not allow for the implant to be positioned in parallel with other abutments. Parallelism is necessary for those prostheses using more than one abutment because the bases of the prosthesis will need to be inserted into respective implanted endosseous implant bodies along parallel axes. Inherent placement discrepancies later found will often make restoration difficult, if not impossible.

In a conventional implanted prosthesis using multiple implant bodies, the prosthesis includes a metal bar or bridge which spans the different implant sites. The dentist conventionally screws the prosthesis into each of the implant bodies until a standard torque is achieved, such as 30 Newtons. Ideally, each of the prothesis abutments is mated perfectly with a corresponding endosseous implant body and there is no tensioning, compressive or torsional force exerted by any of the abutments on the metal bridge. Where one or more of the abutments has been misaligned to their respective endosseous implant bodies, however, as occurs through transfer error between a patient's mouth and a model of same, the metal bridge can be warped upon installation from the position it assumes under no stress. This can happen, for example, when one segment of the metal bridge is bent downward in order to screw a misaligned abutment into an implant body. The stressed metal bridge attempts to spring back to its unstressed shape, exerting a corresponding force on the misaligned abutment and implant body. This spring-tensioning may cause failure of the prosthesis and/or failure of the implant body, which will attempt to migrate to a new unstressed position, causing bone loss.

Parallelism is also necessary to match front tooth or other natural tooth angulation.

Several types of threaded designs such as floating and indirect screws have been proposed to alleviate alignment problems unforseen at the time of implant manufacture. These devices are technically difficult and expensive to install.

In an attempt to accommodate misalignment problems, one conventional implant is offered with a plastic, intentionally loose-fitting press-fit abutment. However, this non-machined abutment will typically not work or fit property in a previously installed internally-threaded endosseous implant body.

Therefore, a need exists for a single implant body that can accommodate both a screw-threaded and a precisely machined press-fit abutment. A need further exists for a method of precise transfer of the reference points of the position of an endosseous implant body between the patient's jaw and a model thereof, such that alignment problems are reduced, thus reducing the possibility of implant prosthetic failure and implant body failure.

SUMMARY OF THE INVENTION

According to one aspect of the invention, a kit for creating and implanting a dental implant at an edentulous site in a jaw of a patient is provided. This kit minimally includes, as one of its components, an endosseous implant body with a receptacle formed therein. A sidewall of the receptacle has screw threads and in addition has a noncircular receiving surface. A first, screw-threaded abutment of the kit has screw threads formed on its stem to mate with the screw threads of the endosseous implant body. A second, press-fit abutment base has at least one noncircular locking surface that mates with the noncircular receiving surface of the endosseous implant body. In this manner, a single endosseous implant body can be used for either type of abutment.

It is preferred that a plurality of such noncircular receiving surfaces be formed in the receptacle of the endosseous implant body, and that such noncircular receiving surfaces be corners of a polyhedron. In one embodiment, the screw-threaded abutment has a nonthreaded terminal section on its stem to assist leading in the screw-threaded abutment into the receptacle of endosseous implant body. The nonthreaded terminal section is machined to be closely received in a nonthreaded section of the implant body receptacle to reduce wobble caused by lateral forces on the implant abutment.

According to another aspect of the invention, the press-fit abutment base of this kit and the endosseous implant body are used in a method for fabricating an endosseous implant. An endosseous implant body is implanted at a site in the jaw of a patient. This is followed by press-fitting an implant abutment base into the implant body such that the abutment base is angularly locked into position with respect to the implant body; reference points defining the position of the implant body are thus transferred to the abutment base. An impression pick-up is then attached to the implant abutment base. An impression of curable material is formed about the site of the implant body so as to adjoin the implant base. Once the impression is cured or hardened, the impression is removed together with the impression pick-up and the abutment base.

Removal of the impression exposes the stem of the implant abutment base. An endosseous implant body replica is press-fit to this stem. Thereafter, a model of the patient's mouth is formed against the impression and around the endosseous implant body replica. Since the noncircular locking surfaces of the abutment base mate with the noncircular receiving surfaces of the replica, the reference points on the endosseous implant body are effectively transferred from the abutment base to the implant body replica, which will form a portion of a model of the patient's mouth. In this way, reference points defining the position of the endosseous implant body relative to the patient's mouth are precisely translated to this model, thereby allowing a precise fashioning of a dental prosthesis on the implant base. The precise transfer of the reference points from the patient's mouth to the model is a principal technical advantage of the invention in that prior art problems of misalignment are largely mitigated. A further technical advantage of the invention inheres in the ability of the endosseous implant to receive both screw-threaded and press-fit abutments.

By using the endosseous implant body of the invention, the dentist does not have to pre-select from two different types of dental implant before surgical placement. The locking press-fit abutment base allows the clinician to plant the implant body into the best available bone and to provide the best possibility for long term success under chewing function; further, this base allows the clinician and laboratory technician to properly align the prosthetic heads for the accurate fabrication of tooth replacement. Implant bodies do not have to be dismantled at each working appointment, thereby reducing the amount of wasted clinical time.

BRIEF DESCRIPTION OF THE DRAWINGS

Further aspects of the invention and their advantages will be discerned with reference to the following detailed description when taken in conjunction with the drawings, in which.

DETAILED DESCRIPTION OF THE INVENTION

Figure 1:
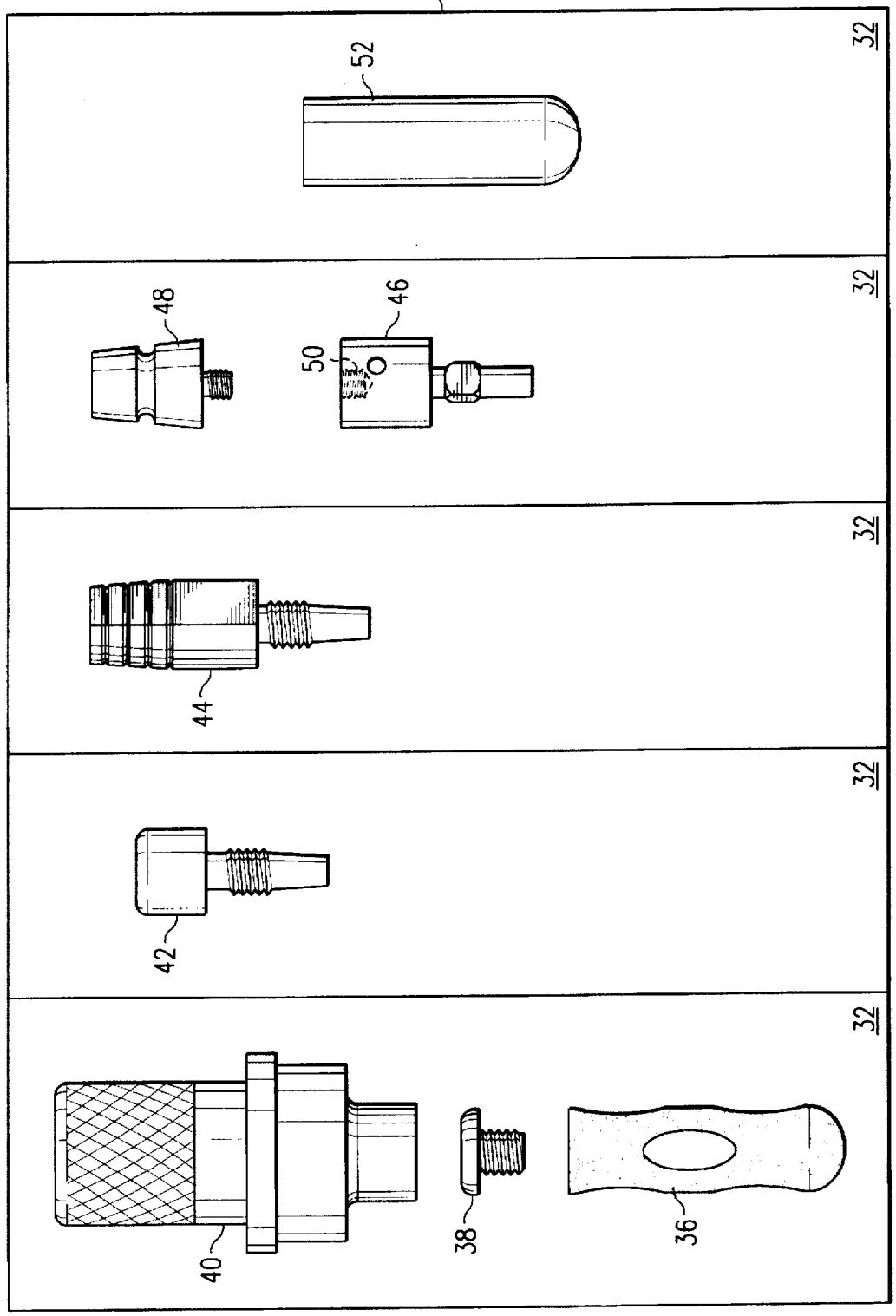
FIG. 1 is a plan view of a surgical prosthetic kit according to the invention.

Referring first to FIG. 1, a dental implant surgical prosthetic kit is indicated generally at 30. The dental kit 30 has a plurality of components which are preferably contained within several pockets 32 of a container 34, which may be a plastic pouch or envelope or the like. Further, many or all of the illustrated components may be further enclosed by hermetically sealed vessels (not shown) which will keep at least those components that will come into contact with the patient's mouth, tissues and structures sterile until use.

The kit 30 includes an endosseous implant body 36 that is adapted for implantation into a patient's jaw. A bone healing screw 38 is adapted to be screwed into a central bore or receptacle of the implant body 36. The implant body 36 and healing screw 38 are placed into a surgical site as a unit (later described) by means of a transfer handle 40.

The kit further contains a gum healing screw 42 which, as will be later described, is used in an intermediate stage of the implanting process.

Importantly, the kit 30 includes each of two different kinds of abutments that are meant to be assembled to the endosseous implant body 36: a screw-threaded abutment 44 and a press-fit abutment base 46. The abutment base 46 is used in conjunction with an impression pick-up 48 which screws into a threaded bore 50 in the abutment base 46. Finally, the kit preferably includes an endosseous implant body replica 52, which has an exterior surface and central receptacle having the same general size and configuration of the endosseous implant body 36.

Figure 2:
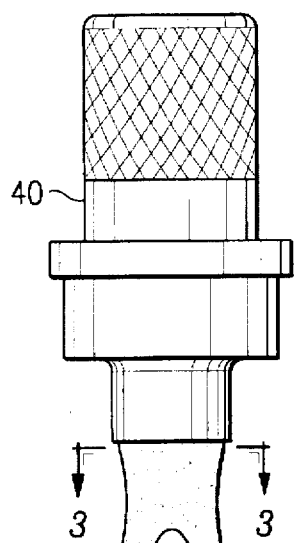
FIG. 2 is an elevational view of an endosseous implant body according to the invention as assembled to a transfer handle.

FIG. 2 is a magnified elevational view of the endosseous implant body 36 as shown engaged by the transfer handle 40. A plurality of dimples 54 are formed in the exterior sidewall of the endosseous implant body 36, which takes a generally cylindrical shape. Dimples 54 are used to increase surface area; other departures from a smooth exterior cylindrical surface can also be used to increase available surface area for bone bonding. The endosseous implant body 36 is preferably formed of titanium or titanium alloy and is then coated with hydroxyapatite (HA) or other material that is biocompatible with bone and promotes the growth of bone around it. The implant body 36's exterior surface may also be plasma-sprayed titanium.

Figure 3:
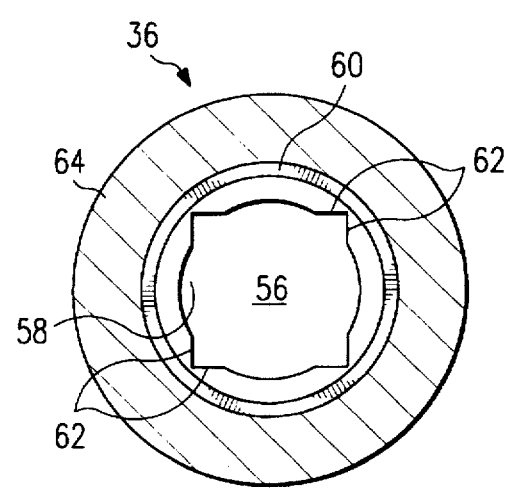
FIG. 3 is a top sectional view taken substantially along line 3—3 of FIG. 2.

As best seen in FIG. 3, a central, coaxial bore or receptacle 56 is formed in the endosseous implant body 36. A sidewall 58 of the receptacle 56 is provided with both screw threads 60 and at least one noncircular receiving surface 62. A lower portion of the sidewall 58 remote from top surface 64 preferably is nonthreaded. In a preferred embodiment, there are a plurality of noncircular receiving surfaces 62, here shown as corners of a polyhedron. The polyhedron used in the embodiment shown in FIGS. 1 and 2 is a cube, although this can be changed to a rectangular prism, other polyhedra, or other noncircular shapes such as those having an elliptical cross-section. A top surface 64 of the endosseous implant body 36 is precisely machined, for example to be flat and smooth, so as to provide a set of reproducible reference points once the endosseous implant body 36 is implanted into the jaw of the patient. The top surface 64 can alternatively be provided with a dimple or other nonflat, machined mating surface.

Figure 4:
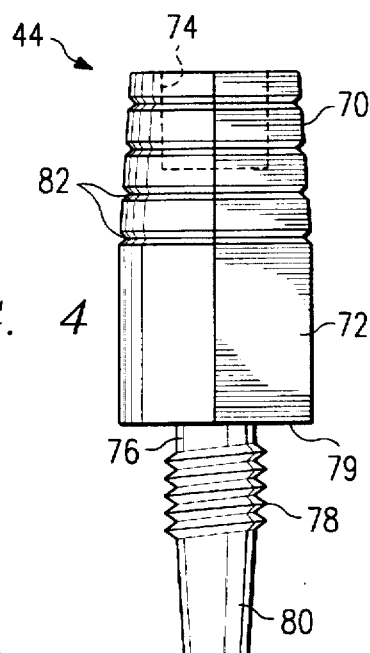
FIG. 4 is an elevational view of a screw-threaded abutment according to the invention.

FIG. 4 is a magnified elevational view of a first, screw-threaded abutment which may be used in conjunction with the endosseous implant body 36. The abutment 44 has a head 70 which includes a pair of flats 72 (one shown) as a reference point locator when used in combination with an impression. The screw-threaded abutment 44 further includes a square-shaped receptacle 74 to permit the twisting of the abutment base 44 into the implant body via a wrench. A stem 76 extends downwardly from a lower end of the head 70 and includes screw threads 78 on a portion thereof that are adapted to engage the screw threads 60 of the endosseous implant body 36. (It should be understood that the terms "up", "down" and the like refer to the components of the invention as they would be oriented to a patient's mandible, and that these directions would be reversed for a prothesis used in a patient's upper jaw.) A lower surface 79 of the head 70 is precisely machined to mate with top surface 64 of implant body 36. A terminal or lowest section 80 of the stem 76 may be tapered for easy indexation of the stem 76 to the endosseous implant body receptacle 56, and such that the threads 78 correctly engage the threads 60 of the endosseous implant body 36 (FIG. 3). Section 80 is machined so as to be closely received by a nonthreaded section of receptacle 56 in implant body 36. The head 70 further includes a plurality of circumferential grooves 82 to provide a gripping surface to the dental prosthesis (not shown) to be formed around the head 70.

Figure 5:
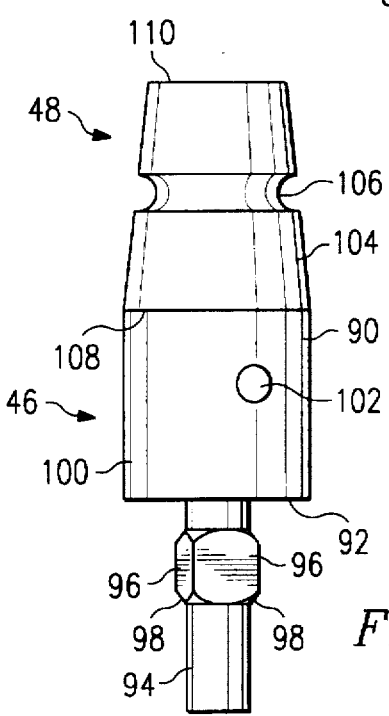
FIG. 5 is an elevational view of a press-fit abutment base according to the invention, as assembled to an impression pick-up.

FIG. 5 is a magnified elevational view of a press-fit abutment base 46 as attached to an impression pick-up 48. The press-fit base 46 includes a head 90 that preferably is cylindrical in shape. The head 90 has a lower surface 92 from which depends a coaxial stem 94. Spaced somewhat below the lower surface 92 of the head and positioned on the stem 94 is at least one noncircular locking surface 96. In the illustrated embodiment, there are four such noncircular locking surfaces 96 that together form a cube. The noncircular locking surfaces 96 are provided with a slight chamfer 98 for a transitional region for ease of indexation to respective noncircular receiving surfaces 62 of the endosseous implant body 36. Alternatively, the locking surfaces 96 can be positioned on the stem to adjoin surface 92 of head 90. The bottom surface 92 of the press-fit implant base is flat and smooth and is machined so as to mate substantially perfectly with the top surface 64 of the endosseous implant body 36, thereby allowing the location in the patient's mouth of a locus of reference points consisting of the top surface 64 of body 36 to be precisely translated to the bottom surface 92 of the abutment base 46. Further, the noncircular receiving surfaces 62 and the noncircular locking surfaces 96 are machined or otherwise formed to very tight tolerances so that there is no play between the two when the locking surfaces 96 are received in the receptacle to be engaged by the receiving surfaces 62; in fact, a small amount of force is required to press-fit the stem 94 into the receptacle 56. The tolerances in general for all machined components are ±0.0001 inch.

A sidewall 100 of the head 90 has a horizontal bore 102 formed therein which opens onto a central coaxial bore. The bore 102 permits the abutment base 46 to accept a cast abutment body on its upper and outer surfaces and within the central bore (see FIG. 6), to thereby create a complete abutment, and forms a sprue vent for the casting process. The abutment base 46 further is cementable. The screw threaded abutment 44 (FIG. 4) and the press-fit abutment base 46 (FIG. 5) are preferably formed of a tough, machinable, inert and refractory substance such as titanium or titanium alloy.

The impression pick-up 48 preferably has a slight taper to its sidewall 104. A substantial circumferential groove or indentation 106 is formed on the sidewall 104 and is spaced upwardly from a lower surface 108 of the impression pick-up 48 by a distance sufficient to allow impression material to securely engage the indentation 106. The impression pick-up 48 is screw-threaded into a threaded receptacle (not shown in FIG. 5) of the press-fit abutment base 46; for this purpose, the impression pick-up 48 is provided with a depending threaded stem (not shown; see FIG. 1). A slot or other appropriate wrench engaging feature may be provided on the top surface 110 of the impression pick-up 48 to aid in threading the impression pick-up 48 into the head 90 of the press fit abutment base 46. The impression pick-up 48 is preferably formed of an inert metal.

Figure 6:
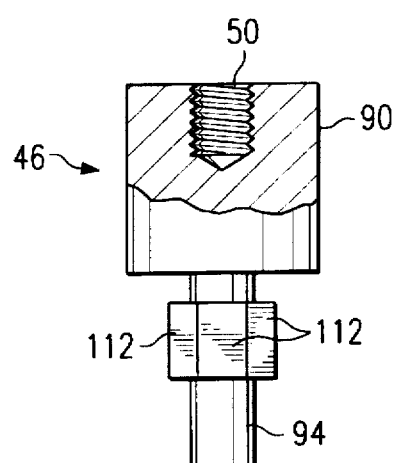
FIG. 6 is an elevational view with parts broken away of a press-fit abutment base with trapezoidal locking surfaces.

FIG. 6 illustrates an alternative embodiment of a press-fit abutment base 46. Instead of the square locking surfaces 96 shown in the embodiment of FIG. 5, the embodiment in FIG. 6 is provided with trapezoidal locking surfaces 112 (3 of 4 shown) that together form four sides of a trapezoidal prism. Any orthogonal cross-section of this prism will show a trapezoid having parallel sides of unequal length. A nonsymmetrical set of locking surfaces 112 (and corresponding set of receiving surfaces; see FIG. 11) is preferred because the dentist and technician then can insert the abutment base into either the endosseous implant body 36 or its replica 52 in only one way. Once inserted into the endosseous implant body, the noncircular locking surfaces 96 or 112 prohibit any twisting or angular translation of the abutment base with respect to the endosseous implant body. This provides a precise mating of the abutment base 46 to the implant body 36 and permits a precise translation of the orientation of the implant body 36 to a model, as will be described below. The head 90 of the press-fit abutment base 46 is provided with a screw-threaded central receptacle 50 which is adapted to receive a threaded stem of the impression pick-up 48 (see FIG. 1).

Figure 7:
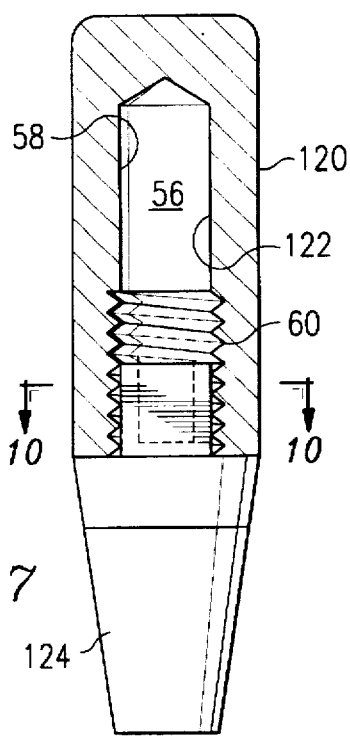
FIG. 7 is a part-elevational, part-sectional view of an endosseous implant body in a second embodiment as assembled to a second embodiment of a press-fit abutment base.
Figure 8:
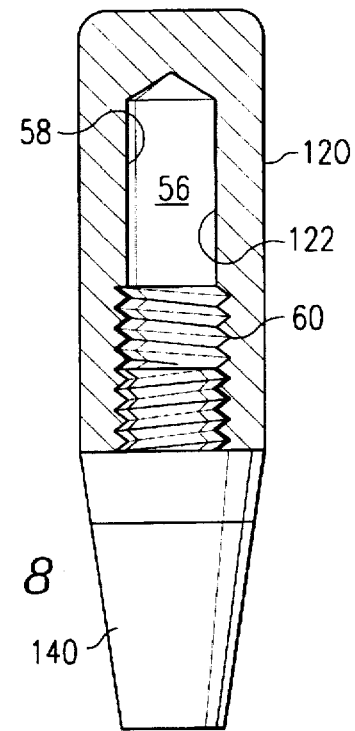
FIG. 8 is a part-elevational, part-sectional view of the endosseous implant body shown in FIG. 7, but as assembled to an alternative embodiment of a screw-threaded abutment.
Figure 9:
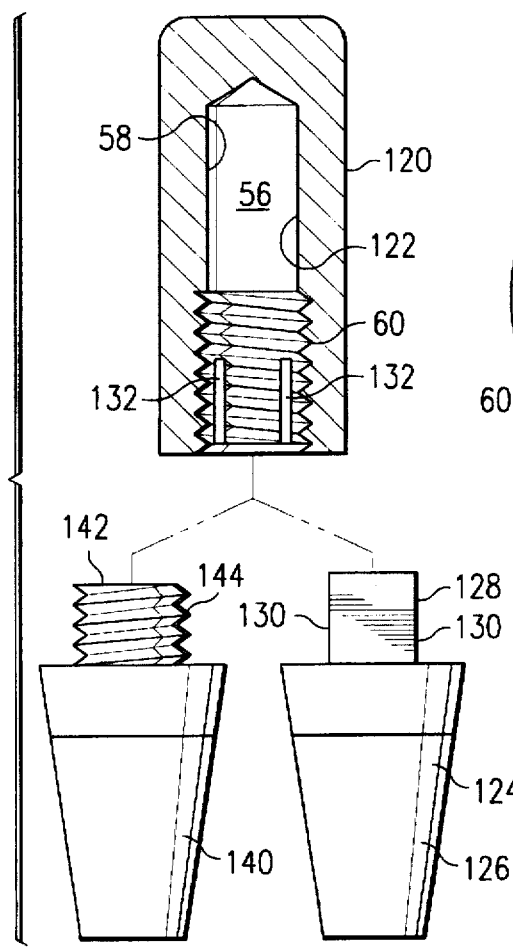
FIG. 9 is an exploded view of the endosseous implant body and abutment bases shown in FIGS. 7 and 8.
Figure 10:
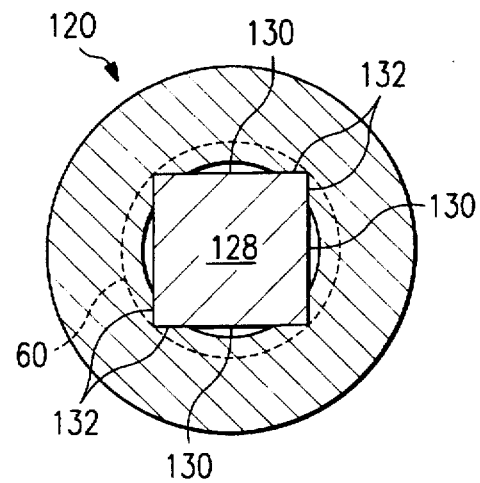
FIG. 10 is a bottom cross-sectional view taken substantially along line 10—10 of FIG. 7.

FIGS. 7–10 illustrate a further embodiment of the invention. A duo-function endosseous implant body 120 has a slightly different shape from implant body 36 (FIGS. 1 and 2). As before, the endosseous implant body 120 has a central receptacle or bore 56 that includes a plurality of female threads 60. The sidewall 58 further includes a nonthreaded portion 122 to receive the smooth terminal portion 80 of the screw-threaded abutment 44 (see FIG. 4) or a like portion of the press-fit abutment base stem (see FIG. 5). As is best seen in FIG. 9, another embodiment of a press-fit abutment 124 has a frustoconical head 126 and a stem 128 that is formed entirely by a polyhedral solid having a plurality of noncircular (in this instance, square) locking surfaces 130. These noncircular locking surfaces 130 are closely received as by an interference fit with a like plurality of noncircular receiving surfaces 132 formed in the sidewall 58 of the receptacle 56. FIG. 7 illustrates the press-fit abutment 124 as fully inserted into the endosseous implant body 120. FIG. 8 shows the same endosseous implant body 120 being used in conjunction with the screw-threaded abutment 140. The abutment 140 has a stem 142 that is provided with a plurality of screw threads 144. These male screw threads engage a like plurality of female screw threads 60 formed in the sidewall 58 of the endosseous implant body 120. As illustrated, the endosseous implant body 120 and the abutments 124 and 140 in FIGS. 7, 8 and 9 are oriented for insertion into the upper jaw of a patient.

Figure 11:
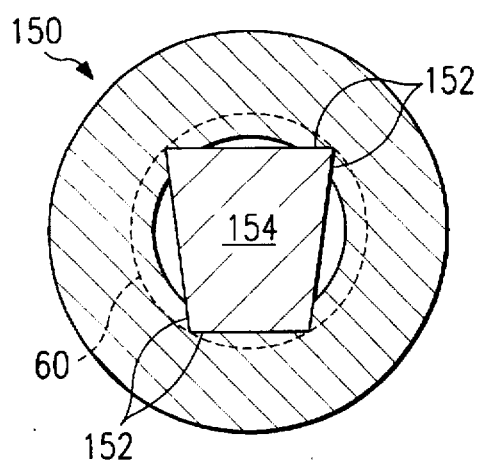
FIG. 11 is a top cross-sectional view of a further embodiment of an endosseous implant body according to the invention and a mating press-fit abutment base with trapezoidal locking surfaces.
Figure 12:
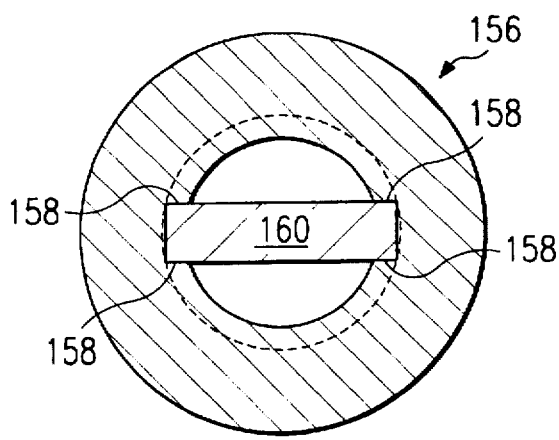
FIG. 12 is a further embodiment of an endosseous implant body and press-fit abutment base according to the invention, wherein the locking surfaces consist of a blade.

FIGS. 11 and 12 are top sectional views illustrate two further embodiments of endosseous implant body/press-fit base combinations. In FIG. 11, an endosseous implant body 150 has a plurality of screw threads 60 as before, and also has a set of noncircular receiving surfaces 152 that are formed as corners of a trapezoid. Also illustrated in this sectional view is a stem 154 of a press-fit abutment base. The stem 154 has at least a portion having a trapezoidal cross-section, so as to present a plurality of locking surfaces 154 that mate with the receiving surfaces 152. As stated previously, an asymmetrical set of locking and receiving surfaces is particularly preferred because such surfaces define one and only one relationship between the endosseous implant body 150 and the press-fit abutment base.

In FIG. 12, a further endosseous implant body 156 is provided in which the noncircular receiving surfaces 158 are opposed channels or slots, such that a thin or blade-like section 160 of a press-fit abutment base stem can be closely received by them. Other noncircular locking and receiving surfaces will occur to those skilled in the art, such as those forming noncubic rectangular prisms, irregular shapes or portions of other polyhedra.

Figure 13:
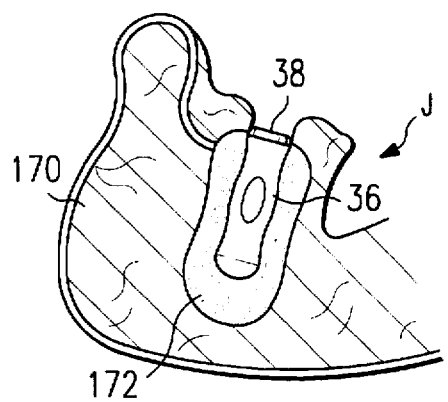
FIGS. 13–29 are views of successive steps of a method of fabricating a dental prosthesis according to the invention.
Figure 14:
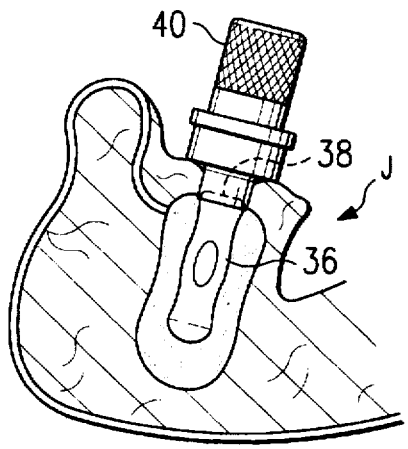
Figure 15:
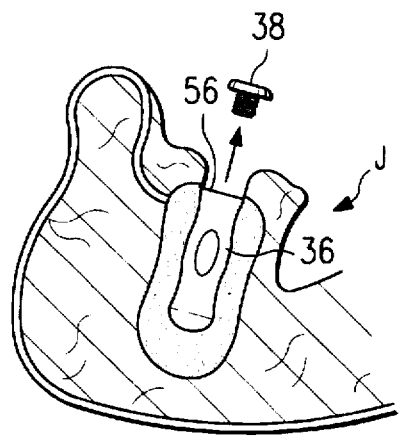
Figure 16:
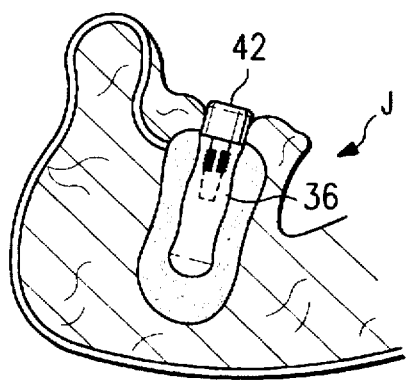

FIGS. 13–29 are views of sequential steps in a dental implant fabrication and implantation procedure according to the invention. FIGS. 13–20 in particular are sectional views of a jaw J at an edentulous site were it is desired to implant a dental prosthesis. In FIG. 13, the facia and soft tissue of the patient's jawbone are indicated at 170 and the mandible thereof is indicated at 172. A receptor site is surgically drilled into the mandible 172 and is trephined to a specific depth and width. The endosseous implant body 36 is then placed into the mandible 172 along with the bone healing cap 38 via the transfer handle 40 (FIG. 14) to prevent occlusion of the receptacle 56 by new bone tissue. The transfer handle 40 is removed. Prior to insertion, the bone healing cap 38 is screwed onto the implant body 36, and the transfer handle 40 is crimped onto the cap 38. After placement of the body 36 and the cap 38 in the surgical site, the transfer handle is popped off of cap 38 by flexing it away from the body-cap axis. The bone is then allowed to heal over a period of time around the endosseous implant body 36. Referring next to FIG. 15, the bone healing cap or screw 38 is removed from the top surface of the endosseous implant body 36. Next (FIG. 16), the gum healing cap 42 is screwed into the endosseous implant body 36 to permit healing of the gum around the surgical site.

Figure 17:
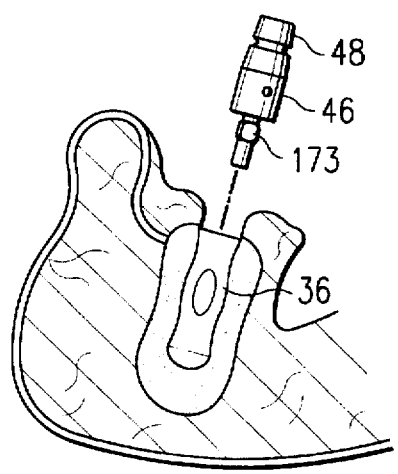
Figure 18:
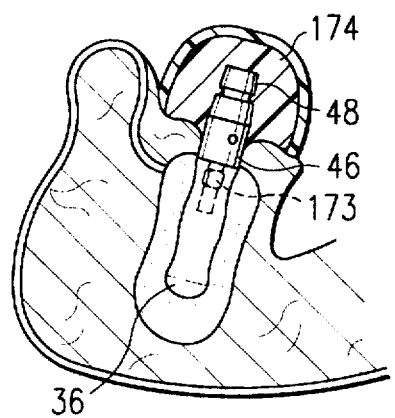

In FIG. 17, there is seen the insertion of a press-fit abutment base 46 into the endosseous implant body 36. As above mentioned, the locking surfaces of the press-fit abutment base and the noncircular receiving surfaces of the endosseous implant body 36 are manufactured to very close tolerances, such that there is no play between the two components. A locking surface 173 is shown in particular to be oriented to the side. The press-fit abutment base at this point has the impression pick-up 48 screwed into its top surface. The combined abutment base 46 and impression pick-up 48 is tapped into place inside the endosseous implant body 36, where it engages the noncircular receiving surfaces thereof.

Next (FIG. 18), an impression 174 is formed inside the patient's mouth to surround this site and possibly other sites as well. The impression, which is of a noncured, moldable material, is formed so as to surround the exposed portions of the press-fit abutment base 46 and the impression pick-up 48. The impression is then allowed to cure or harden.

Figure 19:
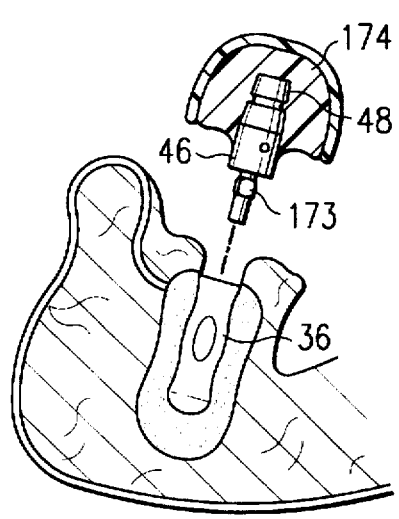

In FIG. 19, the impression 174 is used to lift the press-fit abutment base out of the endosseous implant body 36 with the aid of the impression pick-up 48. Because the impression 174 is a negative template of the region surrounding the edentulous site, the frame of reference or plurality of reference points defining the position of the endosseous implant body 36 in the patient's jaw is directly translated into the position of the press-fit abutment base with respect to the impression 174.

Figure 20:
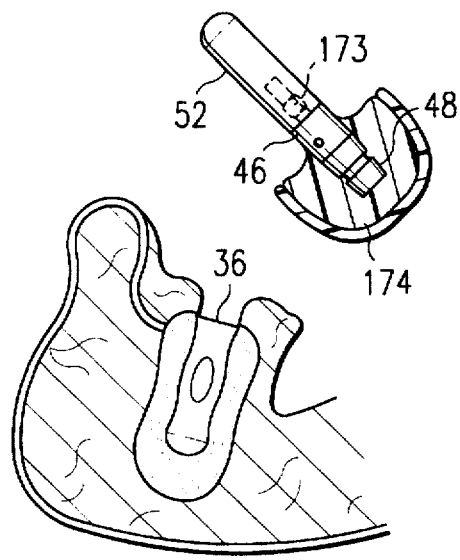
Figure 21:
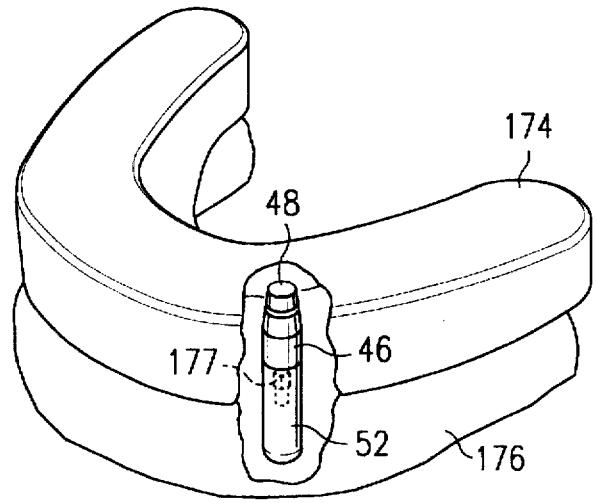

In FIG. 20, the endosseous implant body replica 52 is press-fit onto the stem of the press-fit abutment base 46. Replica 52 has the same noncircular receiving surfaces in it that implant body 36 has, thus allowing a transfer of reference points to it from base 46. The impression 174, when considered as a unit with components 46, 48 and 52, is then ready to be used as a template in constructing a model 176 of the edentulous site and possibly other portions of the patient's jaw (FIG. 21). A locking surface 177 of base 46 is shown oriented to the front. The material forming the model 176 is formed around the endosseous implant body replica 52.

Figure 22:
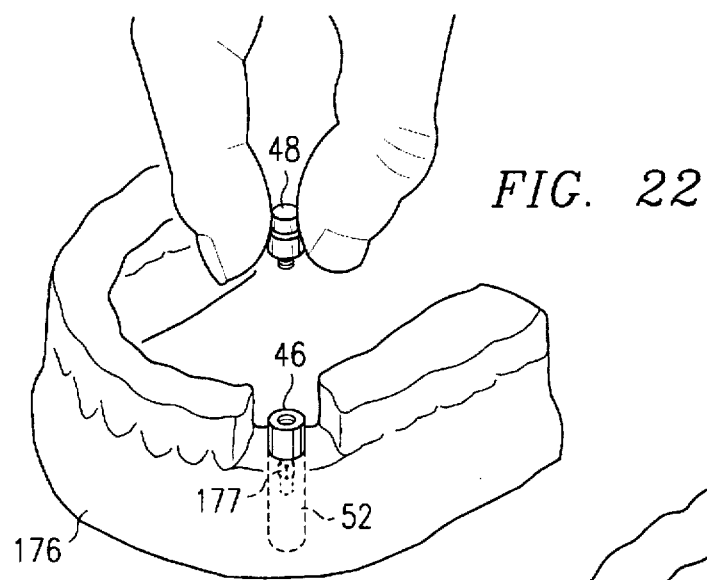
Figure 23:
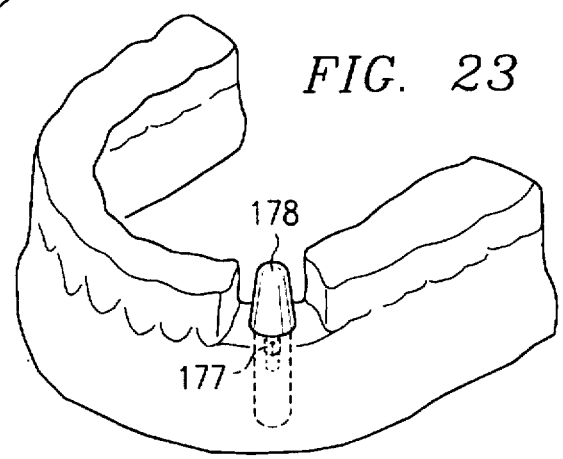
Figure 24:
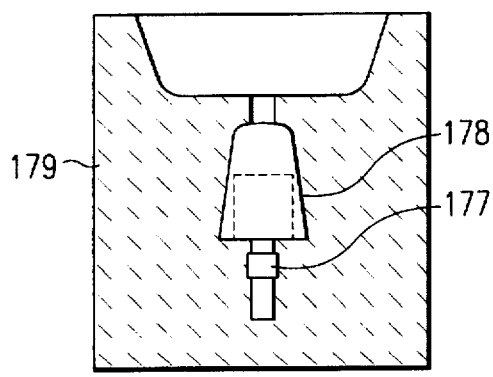
Figure 25:
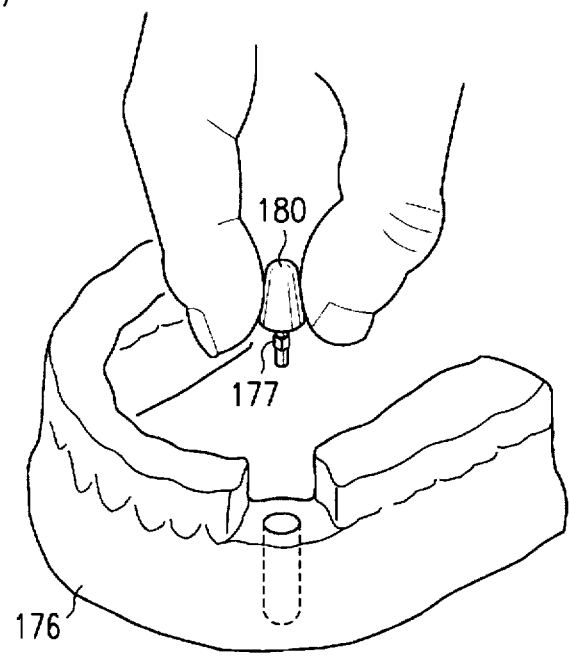
Figure 26:
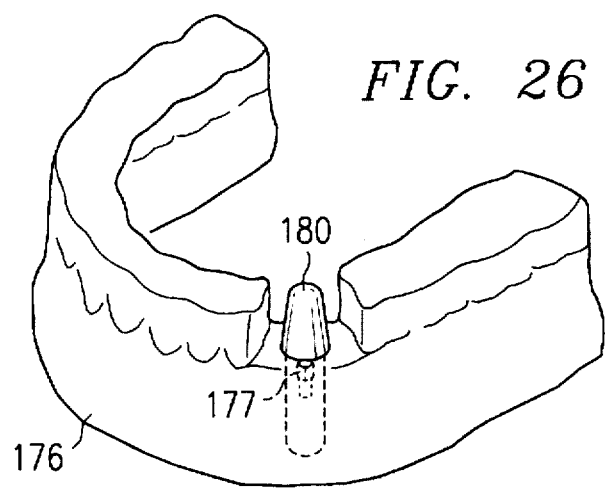
Figure 27:
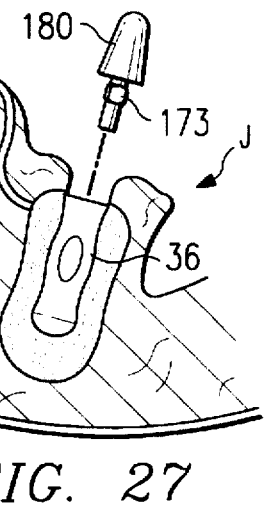
Figure 28:
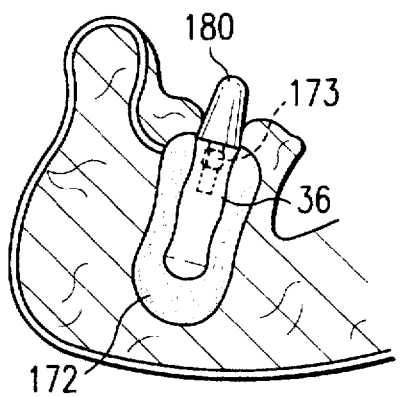
Figure 29:
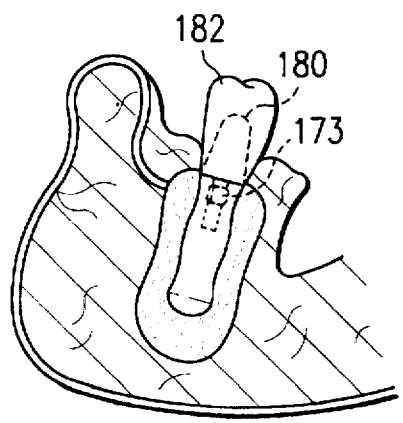

Turning next to FIG. 22, the impression material and the impression pick-up 48 are removed from the model 176, leaving the embedded endosseous implant body replica 52 and the press-fit implant base 46. Then, a wax model 178 of a cast portion of the abutment body is formed on an around the base 46 as is shown in FIG. 23. The abutment is then removed and a stone sprue former 179 is formed around the abutment. The sprue former 179 is used as a lost-wax mold into which gold or other castable metal is introduced. The gold is cast to a remainder of the abutment base 46 in order to create an entire press-fit abutment. In FIG. 25, the abutment 180 is returned to the model 176, as is shown in FIG. 26, again with locking surface 177 facing forward. In FIG. 27, the finished abutment 180 is returned to the patient's jaw J where it is inserted into the endosseous implant body 36. The abutment 180 after insertion is shown in FIG. 28; locking surface 173 has precisely the same orientation as it had during the step shown in FIG. 17. After testing the fit, the abutment 180 is removed and a dental prosthesis 182 is completed around and to include the abutment 180. The completed and implanted dental prosthesis is shown in FIG. 29.

In summary, a novel dental implant system has been shown and described by which the dentist can select screw-threaded or press-fit abutments for installation in an endosseous implant body. The system permits a precise translation of reference points from the patient's mouth to a model such that errors in placement and alignment are obviated.

While illustrated embodiments of the present invention have been illustrated and described, the invention is not limited thereto but only by the scope and spirit of the appended claims.

What is claimed is:

1. A kit for creating and implanting a dental implant at an edentulous site in a jaw of a patient, comprising:

an endosseous implant body having a top surface, a receptacle of said implant body extending downwardly from said top surface, an interior sidewall of said receptacle having screw threads, at least one noncircular receiving surface also formed in said interior sidewall;

a first, screw-threaded abutment having a head and a stem extending downwardly from said head, screw threads formed on said stem to mate with said screw threads of said receptacle in said endosseous implant body; and a second, integral, press-fit castable and cementable abutment base having a head adaptable to have cast thereto an abutment body, a stem of said second base extending downwardly from said head, said stem cementable into and receivable in said receptacle of said implant body as an alternative to said receptacle receiving said stem of said screw threaded abutment, at least one noncircular locking surface formed on said stem to mate with said at least one noncircular receiving surface on said sidewall of said receptacle, such that when said press-fit abutment base is press-fit into said receptacle of said implant body, said press-fit abutment base will not be able to rotate in respect of said implant body.

2. The kit of claim 1, wherein a plurality of noncircular receiving surfaces are formed in said sidewall of said receptacle of said implant body, a like plurality of noncircular locking surfaces formed on said stem of said press-fit abutment base to mate with respective ones of said plurality of noncircular receiving surfaces.

3. The kit of claim 2, wherein said noncircular receiving surfaces and said noncircular locking surfaces are corners and faces of polyhedra, respectively.

4. The kit of claim 3, wherein said polyhedra are rectangular prisms.

5. The kit of claim 3, wherein said polyhedra are trapezoidal prisms, a cross-section of said prisms having parallel sides of unequal length.

6. The kit of claim 1, wherein said stem of said screw-threaded abutment base has an end, a nonthreaded section formed adjacent said end.

7. The kit of claim 6, wherein said nonthreaded section is tapered to assist in leading in said screw-threaded abutment base into said receptacle of said endosseous implant body.

8. The kit of claim 1, and further comprising an endosseous implant body replica, a receptacle of said replica having at least one noncircular receiving surface which is substantially identical to said at least one noncircular receiving surface of said receptacle of said endosseous implant body.

9. The kit of claim 8, wherein said implant body replica has an exterior surface of the same general size and shape as an exterior surface of said endosseous implant body.

10. The kit of claim 1, and further comprising a bone healing cap for affixation to said top surface of said endosseous implant body to allow the bone to heal around said implant body at said site.

11. The kit of claim 1, and further comprising a gum healing cap for affixation to said top surface of said endosseous implant body to allow the gum of the patient to heal around said implant body at said site while still permitting access to the top surface of said implant body thereafter.

12. The kit of claim 1, and further comprising an impression pick-up, means for affixing said impression pick-up to said press-fit abutment base, said impression pick-up configured such that once an impression of at least the site in the patient's mouth is made, the impression will pull the impression pick-up with the impression upon removal of the impression from the patient's mouth, said impression pick-up in turn pulling said press-fit abutment base such that said impression, said impression pick-up and said press-fit abutment base are removed from the patient's mouth as a unit.

13. The kit of claim 12, wherein said press-fit abutment base has a top surface, said means for affixing said impression pick-up to said press-fit base comprising a screw-threaded receptacle in said top surface of said press-fit abutment base, and a threaded stem of said impression pick-up adaptable to be threadedly received by said receptacle in said press-fit abutment base.

14. The kit of claim 12, wherein said impression pick-up has a top surface, a bottom surface and at least one side surface extending between said top surface and said bottom surface, an indentation formed in said at least one side surface adaptable to engage material of said impression such that said impression pick-up will adhere to the impression.

15. An endosseous dental implant body, comprising:
a top and a bottom, at least one exterior sidewall extending from said top to said bottom,
a receptacle formed from said top downwardly toward said bottom, an interior sidewall of said receptacle having screw threads adapted to receive a screw-threaded implant abutment base; and
a plurality of noncircular receiving surfaces formed in said interior sidewall, said noncircular receiving surfaces formed as corners of a trapezoid prism having parallel sides of unequal length.

16. A press-fit, cementable and castable dental implant abutment base, comprising:
a head having a top surface and a bottom surface, at least one sidewall extending between said top surface and said bottom surface, said head adaptable to have cast thereto an abutment body; and
a stem formed integrally with said head and extending downwardly from said bottom surface, at least one noncircular locking surface formed on said stem adaptable to mate with a respective noncircular receiving surface formed on an internal sidewall of an endosseous implant body such that said base is cementable into said implant body.

17. The press-fit implant abutment base of claim 16, wherein said at least one locking surface is formed within tolerances of ±0.0001 inch.

18. The press-fit implant abutment base of claim 16, and further comprising a plurality of noncircular locking surfaces formed on said stem, said noncircular locking surfaces adaptable to mate with respective ones of a like plurality of noncircular receiving surfaces formed on an internal sidewall of an endosseous implant body.

19. The press-fit implant abutment of base claim 18, wherein said noncircular locking surfaces are faces of a polyhedron.

20. The press-fit implant abutment of base claim 19, wherein said polyhedron is a rectangular prism.

21. The press-fit implant abutment of base claim 19, wherein said polyhedron is a trapezoidal prism, a cross-section thereof defining a trapezoid having unequal parallel sides.

22. The press-fit implant abutment base of claim 16, wherein said top surface has formed therein means for attaching said abutment base to an impression pick-up.

23. The press-fit implant abutment base of claim 22, wherein said means comprises a screw-threaded receptacle adaptable to receive a stem of the impression pick-up.

24. The press-fit implant abutment base of claim 22, wherein said means for attaching said abutment base to an impression pickup comprises an orifice formed to extend downwardly from said top surface of said head, a sprue vent formed to communicate said orifice to said sidewall of said head to aid the casting of an abutment body thereto.

25. A kit for creating and implanting a dental implant at an edentulous site in a jaw of a patient, comprising:
an endosseous implant body having a top surface, a receptacle of said implant body extending downwardly from said top surface, an interior sidewall of said receptacle having screw threads, at least one noncircular receiving surface formed in said interior sidewall;
an integral, press-fit castable and cementable abutment base having a head adaptable to have cast thereto an abutment body, a stem of said base extending downwardly from said head, said stem cementable into and receivable in said receptacle of said implant body, at least one noncircular locking surface formed on said stem to mate with said at least one noncircular receiving surface formed in said interior sidewall of said implant body; and
an implant body replica having at least one noncircular receiving surface which is substantially identical to said at least one noncircular receiving surface of said endosseous implant body.

26. The kit of claim 25, wherein said head has a top surface, a bore extending downwardly from said top surface adaptable to receive both an impression pick-up and material of an abutment body that is cast to said head at a point in time after receiving the impression pick-up.

* * * * *

(12) EX PARTE REEXAMINATION CERTIFICATE (8673rd)
United States Patent
D'Alise

(10) Number: US 5,755,574 C1
(45) Certificate Issued: Nov. 22, 2011

(54) ENDOSSEOUS DENTAL IMPLANT AND METHOD OF MANUFACTURE

(76) Inventor: James V. D'Alise, Hinsdale, IL (US)

Reexamination Request:
No. 90/011,006, Jun. 8, 2010

Reexamination Certificate for:
Patent No.: 5,755,574
Issued: May 26, 1998
Appl. No.: 08/469,687
Filed: Jun. 6, 1995

Related U.S. Application Data

(63) Continuation-in-part of application No. 08/232,448, filed on Apr. 21, 1994, now Pat. No. 5,468,149.

(51) Int. Cl.
  *A61C 8/00* (2006.01)

(52) U.S. Cl. ........................................ 433/173; 433/174

(58) Field of Classification Search .................... None
See application file for complete search history.

(56) References Cited

To view the complete listing of prior art documents cited during the proceeding for Reexamination Control Number 90/011,006, please refer to the USPTO's public Patent Application Information Retrieval (PAIR) system under the Display References tab.

*Primary Examiner* — Cary E. Wehner

(57) ABSTRACT

An endosseous dental implant system includes an endosseous implant body which is adaptable to receive either a screw-threaded abutment or a press-fit abutment base. An endosseous implant body replica and an impression pick-up are used in conjunction with the press-fit abutment base to get an exact translation of reference points of the implanted body from the patient's mouth to a model, where a dental prosthesis can be fashioned without prior art alignment problems.

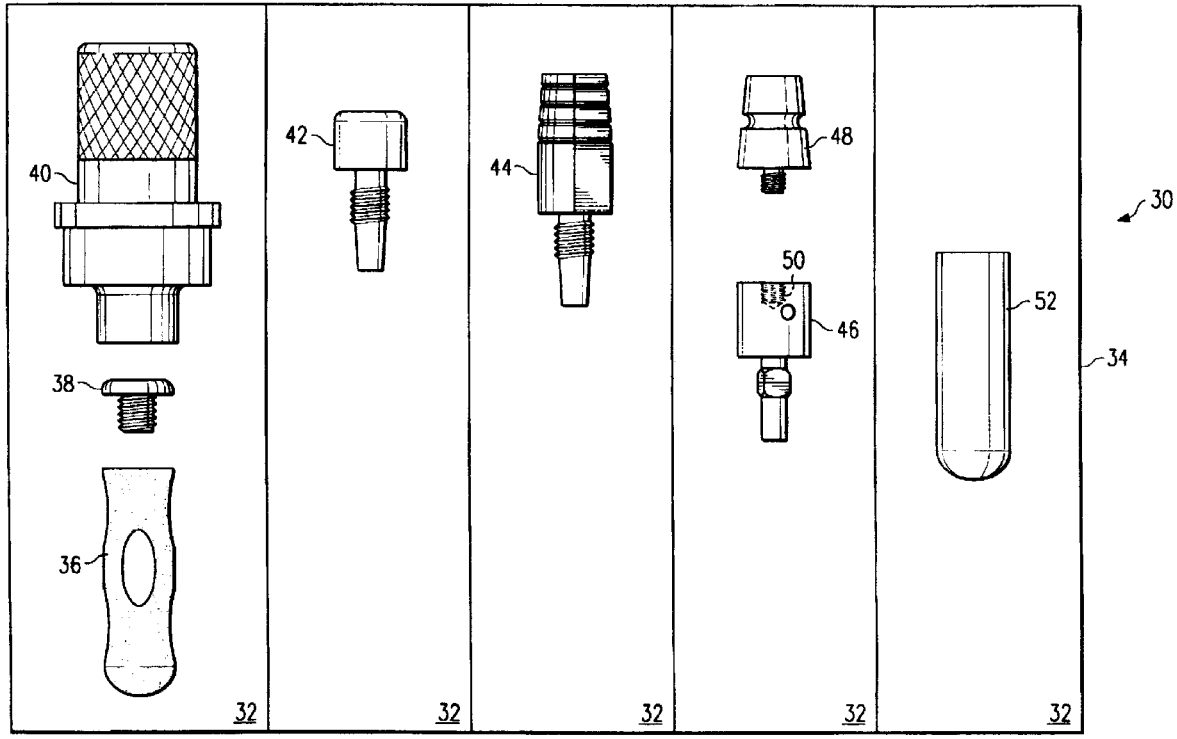

EX PARTE REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

The patentablility of claims 6-9, 14 and 24-26 is confirmed.

Claims 1-5, 10-13 and 15-23 are cancelled.

\* \* \* \* \*